United States Patent [19]

Smith et al.

[11] Patent Number: 4,604,285

[45] Date of Patent: Aug. 5, 1986

[54] PROTEIN C ENZYME DERIVATIVES

[75] Inventors: Richard A. Smith; Robert Cassels, both of Reigate, England

[73] Assignee: Beecham Group p.l.c., England

[21] Appl. No.: 717,269

[22] PCT Filed: Jul. 4, 1984

[86] PCT No.: PCT/GB84/00239

§ 371 Date: Mar. 18, 1985

§ 102(e) Date: Mar. 18, 1985

[87] PCT Pub. No.: WO85/00521

PCT Pub. Date: Feb. 14, 1985

[30] Foreign Application Priority Data

Jul. 20, 1983 [GB] United Kingdom ............... 8319538

[51] Int. Cl.[4] .................... A61K 37/48; C07K 3/08; C12N 9/96; C12N 9/99
[52] U.S. Cl. .................................. 424/94; 435/183; 435/184; 530/380
[58] Field of Search ............... 424/94; 435/183, 184; 260/112 B

[56] References Cited

U.S. PATENT DOCUMENTS 4,285,932  8/1981  Smith .............................. 435/184 X
4,507,283  3/1985  Smith .................................... 424/94

OTHER PUBLICATIONS

J. Clin. Invest. 74, 200-204 (Jul. 1984), Colucci et al.
Blood, 59, No. 5, 1067-1072, (1982), Marlar et al.
Biological Abstracts, vol. 73, 1982, Comp et al, No. 44211.
Biological Abstracts, vol. 74, 1982, Marlar et al, No. 66170.

Primary Examiner—Howard E. Schain
Attorney, Agent, or Firm—Jacobs & Jacobs

[57] ABSTRACT

Known disadvantages of protein Ca are overcome or reduced by acylating the protein to form a derivative which will gradually hydrolyse in vivo to regenerate the active enzyme. The enzyme derivative comprises protein Ca in which the active site essential for anticoagulant activity is blocked by an acyl group removable in vivo by enzymatic hydrolysis to provide a sustained and controlled release of protein Ca, preferred acyl groups being optionally substituted benzoyl or acryloyl groups.

8 Claims, No Drawings

PROTEIN C ENZYME DERIVATIVES

This invention relates to enzyme derivatives, and in particular to derivatives of Protein C which have anticoagulant activity useful in treating thrombotic disorders, such as venous thrombosis. Protein C is a vitamin K dependent plasma protein consisting of two disulphide-linked polypeptide chains, and in order to function as an anticoagulant it must first be activated, according to known methods, to 'activated Protein C', hereinafter referred to as Protein Ca. A disadvantage of Protein Ca as an anticoagulant is that it has a short lifetime in the circulation due to inhibition by an endogenous plasma inhibitor protein.

It has now been discovered that the disadvantages of Protein Ca can be overcome or reduced by acylating the protein to form a derivative in which the anticoagulant activity is masked, but which will gradually hydrolyse in vivo to regenerate the active enzyme. Such acylation will thereby achieve a sustained release action for Protein Ca and chemical control over the kinetics of the anticoagulation process.

Accordingly, the invention provides an enzyme derivative comprising Protein Ca in which the active site essential for anti-coagulant activity is blocked by an acyl group which is removable in vivo by enzymatic hydrolysis to provide a sustained and controlled release of Protein Ca. Preferred acyl groups are optionally substituted benzoyl or acryloyl groups.

Suitable substituted benzoyl groups include those substituted with halogen, amino, $C_{1-6}$ alkylamino, $C_{1-6}$ alkyl, $C_{1-6}$ alkoxy, $C_{2-7}$ alkanoyloxy and/or $C_{2-7}$ alkanoylamino (RCONH-) or alkanoylhydrazino (RCONHNH-). Examples include 4-fluorobenzoyl, 2-, 3-, or 4-toluoyl, 2-, or 4-methoxybenzoyl (i.e. anisoyl), 2-, or 4-ethoxybenzoyl, 2,4-dimethoxybenzoyl, 3,4-dimethylbenzoyl, 4-butylbenzoyl, 3-methyl-4-methoxybenzoyl, 2-acetoxybenzoyl (i.e. acetylsalicyloyl), 2- or 4-aminobenzoyl, and 4-acetamidobenzoyl. Suitable optionally substituted acryloyl groups include $C_{1-6}$ alkyl-acryloyl, furyl-acryloyl, cinnamoyl and $C_{1-6}$ alkyl-cinnamoyl.

The derivatives of the invention may be prepared by reacting Protein Ca with an acylating agent

AB in which A is a locating group which locates the agent in the catalytic site, and B is a acyl group preferably a benzoyl group or acryloyl group as defined above.

Examples of the group A include 4-amidinophenyl and 4-acetamidinophenyl or structurally similar substituted phenyl groups containing a positively charged moiety in the 3- or 4-position.

Examples of suitable acylating agents are: 4-amidinophenyl 4'fluorobenzoate, 4-amidinophenyl 4'-toluate, 4-amidinophenyl 4'anisate, 4-amidinophenyl benzoate, 4-amidinophenyl cinnamate, 4-amidinophenyl 3-(2-furyl)-acrylate, 4-amidinophenyl 2-naphthoate, 4-amidinophenyl 3,3-dimethylacrylate, 4-amidinophenyl 4't-butyl benzoate, 4-amidinophenyl 2',4'-dimethoxybenzoate, 4-amidinophenyl acetylsalicylate, 4-amidinophenyl 4'-ethoxybenzoate, 4-acetamidinophenyl 4'anisate, 4-amidinophenyl 2'-toluate, 4-amidinophenyl 2'anisate, 4-amidinophenyl 3',4'-dimethylbenzoate, 4-amidinophenyl 3'-methyl-4'-methoxy benzoate, 4-amidinophenyl 4'-aminobenzoate, and 4-amidinophenyl 4'-acetamidobanzoate.

The acylating reactions are suitably carried out in aqueous buffered media at a pH range which is not detrimental to the Protein Ca, acylating agent or product, e.g. from pH 6 to pH 9 and preferably at approximately pH 7.

The reaction is generally carried out by mixing the acylating agent with Protein Ca at a moderate temperature. The concentration of acylating agent is preferably 0.05–1.0 mM.

The time for which the reaction is allowed to proceed depends upon the acylating agent employed, and the temperature at which the reaction is carried out. A convenient time is about 0.5 to 1 hour at 0° C. but the reaction may be allowed to continue for longer.

After the reaction is complete the derivative is purified by standard methods such as dialysis, affinity chromatography, and ultrafiltration, and thereafter recovered by standard methods such as freeze-drying from aqueous media. Where necessary the material may be adapted, for example by sterilization, for intravenous administration to human beings.

The acylating agents for use in preparing the derivatives of the invention are either known compounds or can be prepared from known compounds by known methods, such as those disclosed in EP Nos. 9879 and 28489.

The derivatives of this invention are preferably administered as pharmaceutical compositions.

Accordingly the present invention also provides a pharmaceutical composition comprising a derivative of the invention in combination with a pharmaceutically acceptable carrier.

The compositions according to the invention may be formulated in accordance with routine procedures as pharmaceutical compositions adapted for intravenous administration to human beings.

Typically, compositions for intravenous administration are solutions of the sterile derivative in sterile isotonic aqueous buffer. Where necessary the composition may also include a solubilising agent to keep the derivative in solution, and a local anaesthetic such as lignocaine to ease pain at the site of injection. Generally, the enzyme derivative will be supplied in unit dosage form, for example as a dry powder or water-free concentrate in a hermetically sealed container such as an ampoule, sachette or vial indicating the quantity of enzyme in activity units, as well as an indication of the time within which the free enzyme will be liberated. Where the derivative is to be administered by infusion, the derivative will be dispensed with an infusion bottle containing sterile pharmaceutical grade 'Water for Injection'. Where the derivative is to be administered by injection the derivative is dispensed with an ampoule of sterile water for injection. The injectable or infusable composition will be made up by mixing the ingredients prior to administration.

The invention also provides a method of treatment and/or prophylaxis of thrombotic disorders in mammals, including humans, which comprises administering to the mammal an effective amount of an enzyme derivative of the invention.

The quantity of material administered will depend upon the amount of anti-coagulation required and the speed with which it is required, the seriousness of the thromboembolic condition and position and size of a clot if present. The precise dose to be employed and mode of administration must *per force* in view of the nature of the complaint be decided according to the circumstances by the physician supervising treatment. However, in general, a patient will generally receive a daily dose of from 0.05 to 2.0 mg/kg$^{-1}$ of body weight either by injection in up to five doses or by infusion.

The following Examples illustrate the invention.

EXAMPLE 1

Preparation and Reversible Inactivation of Protein Ca (a) Purification of Protein C Protein C can be partially purified from commercial concentrates of vitamin K-dependent human clotting factors.

One vial of concentrate (~100 mg total protein) was dissolved in 20 mM trisodium citrate, pH 6.9 (~15 ml) and run onto a 2×35 cm column of dextran-sulphate-agarose (see below for preparation); the column was then washed thoroughly with 20 mM citrate/pH 6.9 (~375 ml) at a rate of ~30 ml/h until no further protein eluted from it. A gradient of citrate buffer containing an increasing concentration of NaCl (0-1M) was then applied to the column over a period of 8 h. When the NaCl concentration on the column reached ~0.2M, Protein C was eluted and collected as 5 ml fractions. The presence of Protein C was verified by performing a Laurell rocket immunoelectrophoresis assay (Laurell, C. B., Anal. Biochem., 45–52, 15, 1966) in which 5 μl aliquots of selected column fractions were electrophoresed into an agarose gel containing anti-Protein C antibody, those fractions containing Protein C giving rise, after Coomassie-blue-staining for protein, to rocket-shaped immunoprecipitin lines.

Those fractions containing Protein C were pooled and aliquotted out for storage in the presence of 1 mM benzamidine at −40° C.

Dextran-sulphate-agarose was prepared by coupling dextran sulphate to cyanogen bromide-activated Sepharose 4B as descibed by D. S. Pepper and C. Prowse, Thrombosis Res., 687–692, 11, 1977.

(b) Activation of Protein C to Protein Ca

Protein C may be activated to Protein Ca, a serine protease, by incubation with human α-thrombin, the Factor X-activator factor from Russell's Viper venom or trypsin. The activation procedure reduces the MW of Protein C from ~62,000 to ~61,000 by removing an N-terminal dodecapeptide from the heavy amino-acid chain.

The method of activation using thrombin is described below:

A solution of Protein C in 0.1M Tris at pH 8.0, containing 0.1L % bovine serum albumin, was incubated with human α-thrombin (approximately 1/50th of the amount of Protein C).

The progress of the activation procedure may be followed by periodically removing 20λ aliquots of the Protein C-thrombin incubation mixture, neutralisation of the thrombin with a mixture of heparin and antithrombin III (HAT: ~2 μg of each per μg of thrombin) and assaying spectrophotometrically at 405 nm for amidolytic activity by addition of 100 μl of 5 mM substrate S-2238 (H-D-Phe-Pip-Arg-p-nitroanilide) and 880 μl of 0.1M Tris/0.05M NaCl/pH 8.3. After 3-4 h, the activity reached a steady level, and the Protein C was fully activated to Protein Ca.

Thrombin can be removed from Protein Ca solutions either by neutralisation with heparin and antithrombin III, as described above, or by passage of the incubation mixture through a column of sulphopropyl Sephadex C-50; thrombin binds to the column but Protein Ca is eluted by washing with 20 mM MES.Tris/50 mM NaCl/1 mM benzamidine/pH 6.0. Alternatively, insoluble thrombin-Sepharose can be used to activate Protein C, in which case removal of thrombin is effected simply by centrifuging gently.

(c) Measurement of Protein Ca anticoagulant activity

Protein Ca proteolyses Factors V and VIII, thereby blocking the in vivo production of thrombin by both the extrinsic and intrinsic coagulation pathways. This effect can be studied in vitro by means of the kaolin-cephalin clotting time (KCCT) assay (Austen, D. E. G., & Rhymes, I. L; "A Laboratory Manual of Blood Coagulation", Blackwell Scientific Publications, Oxford, 1975), performed as follows:

A sample of activated Protein C, the thrombin having been *exactly* neutralised by heparin-antithrombin III or otherwise removed, was diluted 100× with 0.05M Tris/0.1M NaCl/0.1% BSA*/pH 7.5, and 4×100 μl aliquots of this were added to 4×100 μl aliquots of fresh pooled human plasma at 37° C. One-hundred μl aliquots of a commercially-available kaolin-platelet substitute (chloroform extract of brain) suspension were added, and the 4 mixtures were incubated for exactly 2 min. One-hundred μl aliquots of 0.02M CaCl$_2$ were then added, and the times taken for the plasma to clot noted. This may be conveniently performed using an automated coagulometer.

*Bovine Serum Albumin

When 100 μl of ~0.05M Tris.HCl/0.1M NaCl/0.1% BSA/pH 7.5 was used instead of activated Protein C, a normal physiological value of the KCCT was obtained, lying in the range 45–55 sec. Any significant prolongation of this value, in combination with corroborating evidence from the Laurell immunoelectrophoresis assay and measurements of amidolytic activity, indicates the presence of active Protein Ca.

(d) Formation and deacylation of 4-anisoyl Protein Ca

Fifty μl of HAT-treated, thrombin-activated crude concentrate were incubated at 37° C. in the presence of 500 μM APAN for 1 h (the incubation may be monitored by removing aliquots at intervals and assaying for amidolytic activity using S-2238). The mixture was then diluted to a volume of 100λ by addition of 0.05M Tris.HCl/0.1M NaCl/pH 7.5, and passed through a 0.75×5 cm column of Sephadex G-25 (using $^{125}$I-bovine serum albumin as a protein tracer) in order to remove excess APA, which interferes with the KCCT assay. The eluted acylated protein was diluted to a total volume of 1 ml. In the KCCT assay, this solution behaved as shown in Table 1, having a KCCT value lying within the normal range, i.e. the protein Ca having been inactivated by APAN treatment. Activated concentrate that had not been incubated with APAN showed a prolonged KCCT.

Deacylation of the anisoyl-Protein Ca was effected by incubation with 200 mM hydroxylamine (72 h at 4° C., pH 8.0), which partially restored the anticoagulant and amidolytic activities of Protein C.

TABLE 1

| Effect of acylation by APAN and deacylation by hydroxylamine on the anticoaqulant activity of Protein Ca | |
|---|---|
| Sample | KCCT (sec) |
| concentrate + thrombin + HAT III | 73.5 |

TABLE 1-continued

Effect of acylation by APAN and deacylation by hydroxylamine on the anticoaqulant activity of Protein Ca

| Sample | KCCT (sec) |
|---|---|
| concentrate + thrombin + HAT III + APAN | 51.0 |
| concentrate + thrombin + HAT III + H$_2$NOH | 75.0 |
| concentrate + thrombin + HAT III + APAN + H$_2$NOH | 64.5 |

Abbreviations
HAT: Heparin and antithrombin
APAN: 4-amidinophenyl 4'-anisate

EXAMPLE 2

A general method for the preparation and kinetic characterisation of acyl derivatives of Protein Ca (1) Acylation Protein Ca solutions (2.475 ml in 50 mM sodium phosphate/1 mM benzamidine/0.03% sodium azide/pH 6.9, prepared as in Example 1) were incubated with 25 $\mu$l of acylating agent (50 mM in DMSO) for 2–16 h (depending on the agent used) at 0° C. A control sample, to which 25 $\mu$l of DMSO alone had been added, was also prepared. The extent of acylation was monitored by withdrawing aliquots at intervals and measuring amidolytic activity against S-2238 as described below. When the residual activity was <5% of the control value, excess acylating agent was removed by passage through a Sephadex ®G-25 column equilibrated with 0.1M Tris/20% v/v glycerol/0.9% saline/pH 7.4 (TGS buffer) and elution into 3.5 ml of the same buffer. The solutions were stored on ice and used within 5 min.

(2) Determination of deacylation rate constants

The acylated and control samples were incubated at 37° C. and aliquots removed at intervals (beginning at t=0) to assay amidolytic activity (50 $\mu$l Ca+500 $\mu$l 1 mM S-2238 in 0.1M Trien/0.03% sodium azide/pH 8). Deacylation rates were calculated by linear regression from a pseudo first-order rate plot of $$\log_e\left\{1 - \frac{(A_t - A_o)}{(A_{max} - A_o)}\right\} \text{ vs. time,}$$

where $A_o$ is the activity of the acyl-Ca before incubation at 37° C., $A_t$ is the activity at time t and $A_{max}$ is either:

(i) the maximum activity regenerated after incubation of the acylated Ca for, e.g., 16 h at 25° C. (for fast deacylation, where $k_3 \geq 2 \times 10^{-4} \text{ S}^{-1}$) or (ii) the activity of the non-acylated control sample (for slow deacylation, where $k_3 \leq 2 \times 10^{-4} \text{ S}^{-1}$)

(3) Results

Table 2 summarises the results of three deacylation rate constant determinations on each of six substituted benzoyl derivatives of Protein Ca. As with other serine proteases (see e.g. Wang C—C and Shaw E, Arch. Biochem. Biophys., 259–268, 150, 1972), the deacylation rate constant was found to correlate with the Hammett Sigma constant for para-substituted derivatives. Electron-releasing substituents slowed the deacylation and electron-withdrawing ones accelerated hydrolysis. The slope of the loge (deacylation rate constant)/$\sigma$p plot was found to be 3.16 (correlation coefficient 0.99) which is similar to that found for benzoyl trypsins (Wang & Shaw, loc. cit.) but greater than that shown by acylated fibrinolytic enzymes (A. J. Garman, G. S. Morgan and R. A. G. Smith, to be published).

(4) Conclusion

The data show that a variety of acylated derivatives of Protein Ca can be prepared and deacylated with retention of amidolytic activity. The structure-activity relationship provides a useful degree of predictability for kinetic behaviour.

TABLE 2

Deacylation rate constant data for Protein Ca acylated derivatives

| Benzoyl substituent | $k_3$ (S$^{-1}$) | Linear regression correlation coefficient | Av. $k_3$ (S$^{-1}$) | Hammett $\sigma$P | $t_{\frac{1}{2}}$ (min) |
|---|---|---|---|---|---|
| 4-F | 1.25 × 10$^{-3}$ | 0.997 | 1.21 × 10$^{-3}$ | +0.06 | 10 |
|  | 1.27 × 10$^{-3}$ | 0.996 |  |  |  |
|  | 1.10 × 10$^{-3}$ | 0.998 |  |  |  |
| —H | 1.63 × 10$^{-3}$ | 0.997 | 1.67 × 10$^{-3}$ | 0 | 7 |
|  | 1.71 × 10$^{-3}$ | 0.982 |  |  |  |
|  | 1.67 × 10$^{-3}$ | 0.998 |  |  |  |
| 4-CH$_3$ | 3.43 × 10$^{-4}$ | 0.998 | 3.19 × 10$^{-4}$ | −0.17 | 37 |
|  | 3.43 × 10$^{-4}$ | 0.999 |  |  |  |
|  | 2.70 × 10$^{-4}$ | 0.997 |  |  |  |
| 4-OCH$_3$ | 1.38 × 10$^{-4}$ | 0.996 | 1.45 × 10$^{-4}$ | −0.32 | 80 |
|  | 1.41 × 10$^{-4}$ | 0.998 |  |  |  |
|  | 1.56 × 10$^{-4}$ | 0.995 |  |  |  |
| 4-NH$_2$ | 8.70 × 10$^{-6}$ | 0.992 | 8.37 × 10$^{-6}$ | −0.66 | 1,381 |
|  | 8.27 × 10$^{-6}$ | 0.999 |  |  |  |
|  | 8.15 × 10$^{-6}$ | 0.994 |  |  |  |
| 2-NH$_2$ | 8.50 × 10$^{-6}$ | 0.999 | 8.21 × 10$^{-6}$ | — | 1,444 |
|  | 6.47 × 10$^{-6}$ | 0.986 |  |  |  |
|  | 9.67 × 10$^{-6}$ | 0.968 |  |  |  |

EXAMPLE 3

Demonstration of essentially full recovery of anticoagulant activity after deacylation of 4-toluoyl-Ca at 37° C.

(1) Method 4-toluoyl-Ca, 3.5 ml in TGS buffer, pH 7.4, was prepared as described in Example 2 and, together with 3.5 ml of a non-acylated control, was held at 0° C.

The KCCT values of both samples were measured (in quadruplicate) four times using an automated four-tube coagulometer.

Both samples were then incubated at 37° C. for 3.5 H and the KCCT values were re-determined.

(2) Results

The results are shown in Table 3. KCCT times (the average of 4×4 measurements) are quoted in seconds, relative to the KCCT time for TGS alone (73.5–83.5 sec); they are therefore *prolongations* above the normal.

Also shown are the amidolytic activities of the samples, in SU/ml, measured using 1 mM S-2238 as described in Example 2.

(3) Conclusions

The data (exemplified by the 4-toluoyl derivative) show that acylation of active Protein Ca abolishes both the amidolytic and anti-coagulant activities of the enzyme, and that these activities are fully regenerated after complete hydrolysis of the acyl derivative. The acylation is therefore reversible and affords temporary protection of the whole of the active site function responsible for the physiological (anticoagulant) activity of the enzyme.

TABLE 3

Regeneration of anticoagulant activity from 4-toluoyl Protein Ca

|  |  | Activated partial thromboplastin time (KCCT) (secs) | Amidolytic activity* (S-2238) |
|---|---|---|---|
| t = 0 0° C. | 1. 4-toluoyl-Ca | 7.0 | 94 |
|  | 2. Control Ca | 118.0 | 1,263 |
|  | 3. 1 as % of 2 | 5.9 | 7.4 |
| t = 3½ h 37° C. | 1. 4-toluoyl-Ca | 82.5 | 923 |
|  | 2. Control Ca | 87.0 | 941 |
|  | 3. 1 as % of 2 | 94.8 | 98.1 |

*$\Delta$O.D$^{1\ cm}_{450\ nm}$ min$^{-1}$ × 10$^{-3}$

We claim:

1. An enzyme derivative comprising Protein Ca in which the active site essential for anti-coagulant activity is blocked by an acyl group which is removable in vivo by enzymatic hydrolysis to provide a sustained and controlled release of Protein Ca.

2. An enzyme derivative according to claim 1 wherein the acyl group is an optionally substituted benzoyl or acryloyl group.

3. An enzyme derivative according to claim 2 wherein the acyl group is a benzoyl group optionally substituted by halogen, amino, $c_{1-6}$ alkylamino, $C_{1-6}$ alkyl, $C_{1-6}$ alkoxy, $C_{2-7}$ alkanoyloxy and/or $C_{2-7}$ alkanoylamino.

4. An enzyme derivative according to claim 3 wherein the benzoyl group is
    4-fluorobenzoyl, 2-, 2-, or 4-toluoyl, 2-, or
    4-methoxybenzoyl (i.e. anisoyl), 2-, or
    4-ethoxybenzoyl, 2,4-dimethoxybenzoyl,
    3,4-dimethylbenzoyl, 4-butylbenzoyl, 3-methyl-4-methoxybenzoyl, 2-acetoxybenzoyl
    i.e. (acetylsalicyloyl), 2- or 4-aminobenzoyl or 4-acetamidobenzoyl.

5. A process for the preparation of an enzyme derivative according to claim 1 which process comprises reacting Protein Ca with acylating agent AB in which A is a locating group which locates the agent in the catalytic site, and B is an acyl group.

6. A process according to claim 5 wherein the group A is 4-Amidinophenyl or 4-acetamidinophenyl.

7. A pharmaceutical composition comprising an enzyme derivative according to claim 1 in combination with a pharmaceutically acceptable carrier.

8. A method of treatment and/or prophylaxis of thrombotic disorders in mammals, including humans, which comprises administering to the mammal an effective amount of an enzyme derivative according to claim 1.

* * * * *